(12) United States Patent
Raoult et al.

(10) Patent No.: US 7,166,430 B2
(45) Date of Patent: Jan. 23, 2007

(54) SEQUENCE OF THE TROPHERYMA WHIPPELII BACTERIA RPOB GENE AND OLIGONUCLEOTIDE FOR MOLECULAR DIAGNOSIS OF WHIPPLE'S DISEASE

(75) Inventors: Didier Raoult, Marseille (FR); Michel Drancourt, Marseille (FR)

(73) Assignee: Universite de la Mediterranee (Aix-Marseille II), Marseille (FR)

( * ) Notice: Subject to any disclaimer, the term of this patent is extended or adjusted under 35 U.S.C. 154(b) by 0 days.

(21) Appl. No.: 10/477,915

(22) PCT Filed: May 21, 2002

(86) PCT No.: PCT/FR02/01698

§ 371 (c)(1),
(2), (4) Date: Nov. 18, 2003

(87) PCT Pub. No.: WO02/095033

PCT Pub. Date: Nov. 28, 2002

(65) Prior Publication Data

US 2004/0137459 A1 Jul. 15, 2004

(30) Foreign Application Priority Data

May 21, 2001 (FR) .................................. 01 06641

(51) Int. Cl.
 *C12Q 1/68* (2006.01)
(52) U.S. Cl. .................. 435/6; 536/23.7; 536/24.1; 536/24.3; 536/24.32; 536/24.33; 435/91.1; 435/91.2
(58) Field of Classification Search .............. 435/6, 435/91.1, 91.2; 536/23.7, 24.1, 24.3, 24.32, 536/24.33
See application file for complete search history.

(56) References Cited

U.S. PATENT DOCUMENTS 6,074,865 A1 6/2001 Kelly et al.

FOREIGN PATENT DOCUMENTS

FR 2791357 * 5/1999
WO WO 00/58440 10/2000

OTHER PUBLICATIONS

Drancourt et al. Submitted. Mar. 8, 2000. Genbank Accession No. AF243072.*
Hinrikson et al., "Detection of Three Different Types of 'Tropheryma Whippelii' Directly from Clinical Specimens by Sequencing, Single-strand Conformation Polymorphism (SSCP) Analysis and Type-specific PCR of their 16S-23S Ribosomal Intergenic Spacer Region," *International Journal of Systematic Bacteriology*, vol. 49, pp. 1701-1706, 1999.
Raoult et al., "Cultivation of the Bacillus of Whipple's Disease," *The New England Journal of Medicine*, vol. 342, No. 9, pp. 620-625, Mar. 2000.
Klenk et al., "DNA-dependent RNA polymerase subunit B as a Tool for Phylogenetic Reconstructions: Branching Topology of the Archael Domain," *Journal of Molecular Evolution*, vol. 38, pp. 420-432, 1994.
Drancourt et al., "rpoB Sequence Analysis of Cultured Tropheryma Whippelii," *Journal of Clinical Microbiology*, Vo. 39, No. 7, pp. 2425-2430, Jul. 2001.
Andrew Chin, "On the Preparation and Utilization of Isolated and Purified Oligonucleotides," University of North Carolina School of Law, Mar. 9, 2002. Abridged version.

* cited by examiner

*Primary Examiner*—Jennifer E. Graser
(74) *Attorney, Agent, or Firm*—Oliff & Berridge, PLC.

(57) ABSTRACT

The invention concerns the total sequence of the Tropheryma whippelii bacteria rpoB gene, characterized in that it consists of the nucleotide sequence SEQ ID no. °9, and the nucleotide sequences derived from said sequence specific of the *Tropheryma whippelii* bacteria and their use as probe and primer.

18 Claims, 2 Drawing Sheets

SEQUENCE LISTING

```
<160> NUMBER OF SEQ ID NOS: 24

<210> SEQ ID NO 1
<211> LENGTH: 19
<212> TYPE: DNA
<213> ORGANISM: Artificial sequence
<220> FEATURE:
<223> OTHER INFORMATION: Description of the artificial sequence:
      oligonucleotide

<400> SEQUENCE: 1
tnatgggnnc naanatgca                                                    19

<210> SEQ ID NO 2
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 2
gcccancatt ccatntcncc                                                   20

<210> SEQ ID NO 3
<211> LENGTH: 610
<212> TYPE: DNA
<213> ORGANISM: Tropheryma whippelii

<400> SEQUENCE: 3
gagtcccctg gtcggcacag gtatggagcg gtatgtagcg atcgatgcgg gtgatgtttt       60
aattgccgag gatccgggca ttgtggggga tgtttccgct gatgttgtca ctgtcaagca      120
ggatgacggg aaacatcgcg actaccatgt tggtaaattt gttcgttcaa atcagggcaa      180
ctgttacaac cagcnagttg tggtccgatc cggagatcgt gtataaaaag gtacagttct      240
tgcacatggt ccatgtactg acaaaggtga gcttagtctt ggtagaaatc ttctggttgc      300
tttcatgccc tgggagggct ataactttga ggatgcgata attatcagcc agaatttggt      360
caaggacgac acccttctcnt caatccacat agaagaacat gaggttagca cccgggatac      420
gaagctgggc agtgaagaaa taacgcgaga ccttccgaat gtaagcatgg attacataaa      480
ggacttggac gaacggggta ttatccggat tggcgctgag gttggccctg gggacatttt      540
ggttggtaag gtgaccccaa agggcgagac cgaactcagc gcggaagagc gtttgctgag      600
ggctatcttt                                                             610

<210> SEQ ID NO 4
<211> LENGTH: 2750
<212> TYPE: DNA
<213> ORGANISM: Tropheryma whippelii

<400> SEQUENCE: 4
```

-continued

```
atcccccata gaagattcgg ctggcaatat gcagcttaat ttctccaagc cggttctgga      60
ggccgaagag ttgagcgtaa gggaatgccg tgttcgaggc aggacctatt cggcgcccct     120
gtatgttgag gccgagttca tgaatcatga tacgggcgag ataagactca gacggttttt     180
atggcgatt tcccgcttat gactgacaag ggtacattcg tcataaacgg caccgagaga      240
gttgttgtct ctcagcttgt tcgcagccct ggtgtttatt ttgagcgcac gccggaaaaa     300
aacagtgaaa aggatctttt ttcgggcaga ataatccccg ctcgcggtgc ttggctagaa     360
ttcgaagttg acaggcatga ccagcttggc gttaggttg acaggaagcg caggcagccg      420
gttattttct ttctgagagc aattggcatg actgatgatg atcagggga tgcatttggc      480
gagtttgaat caataagcgt ccagcacgaa aagaatattg ggctgtccag agatgacgcg     540
ctccgggaaa tataccgtcg cgttcgtccg ggggagcagg catcggctga ggctgggcgt     600
gcactcttag agaatttta ctttaccagc agacgttttg acctggcaag ggttggaagg      660
tacaaagtaa atcgcaaact cggtgttgat gttgatccaa ctcggatggt tcttacgagg     720
tcggatatta tcgcaacaat tcgttatctc gcggccttgc atctcggttt ctccgaggtt     780
gcggtgctaa acagcaacaa gagtgtacca atttcaaccg atgatattga ccatcttggt     840
aataggcgca ttagaccggt tggtgagttg gtgcaaaacc agctccgggc tggtctggcc     900
agaatggagc gggttgtgag agagcgcatg acaacccagg atatagaggc gattatcccg     960
cagacactca taaatgtcat gccaattgtt gcagcgctga aggagtttta tggcaccagc    1020
cagctctcgc agtttatgga tcagaataac ccccttgccg gccttacgca aagaggcgc     1080
ttgtcagctc ttggccccgg tggactgtcc cgcgaacgtg ccggtgttga ggttcgagac    1140
gtaaatccca gtcattacgg caggatgtgt ccgatcgaaa ccccagaagg tccaaatatt    1200
ggccttatag ggtctttagc gtgctattcc agggtgaaca gtttcggctt tatagaaacc    1260
ccatatagac gtgttgtcaa cggaaaagtc acagacgata ttgagtatat gacagcaaca    1320
caggaagatg agcatgcgat tgcccaggca agcactccgc tgcgaccgga caactcgttt    1380
gttgatgagc gtgttctggt tcgccgaaaa ggtggagagg tcgaggttgt accggccgat    1440
caggttgatt atatggatgt gtctggacgt cagatggtgt ctgttgcaac ttcgcttata    1500
cccttccttg aacataatga cgctaaccgt gctctcatgg gatcgaatat gcagagacag    1560
gctgtaccac ttctggttac ggagagtccc ctggtcggca caggtatgga gcggtatgta    1620
gcgatcgatg cgggtgatgt tttaattgcc gaggatccgg gcattgtggg ggatgtttcc    1680
gctgatgttg tcactgtcaa gcaggatgac gggaaacatc gcgactacca tgttggtaaa    1740
tttgttcgtt caaatcaggg caactgttac aaccagcnag ttgtggtccg atccggagat    1800
cgtgtagaaa aaggtacagt tcttgcacat ggtccatgta ctgacaaagg tgagcttagt    1860
cttggtagaa atcttctggt tgctttcatg ccctgggagg ctataactt tgaggatgcg     1920
ataattatca gccagaattt ggtcaaggac gacacccttt cgtcaatcca catagaagaa    1980
catgaggtta gcacccggga tacgaagctg ggcagtgaag aaataacgcg agaccttccg    2040
aatgtaagca tggattacat aaaggacttg gacgaacggg gtattatccg gattggcgct    2100
gaggttggcc ctggggacat tttggttggt aaggtgaccc caagggcga gaccgaactc     2160
agcgcggaaa gcgtttgct gagggctatc tttaacgaga agagcatgga ggttcgcgac    2220
acaagtttga aggtcccaca cgggcagcag gggaccgtaa tcgatgttaa gttgtttgat    2280
gcggttgacg gtgaagataa gctgggtgcc ggcataaatc agcggggttgt tgtgtacata    2340
gcgcataagc gcaagattac ggagggagat aagcttgctg ggcgccatgg caacaagggt    2400
```

-continued

```
gttatttcaa agatccttcc ggtagaggat atgcccttca tgctgatgg gaccccccgtt    2460 gatataatcc ttaatccgct cggcgtgccc gcgcgtatga acttcgggca ggttttggaa    2520
acccatttgg ggtggatctc taagcaagga tggaaaatag agggtgatcc tgattgggca    2580
aaagatattc gggtgcgcga ggcgcagcct gatagtaggg tttcaagtcc ggttttgat     2640 ggaatttccg aaggggagat aaccgggctt ttttcttctg tatttccaaa ccgtgatggt    2700
gagcgtgctg tcggttctga tggtaaggct attctctatg atggccgcac               2750
```

<210> SEQ ID NO 5
<211> LENGTH: 20
<212> TYPE: DNA
<213> ORGANISM: Artificial sequence
<220> FEATURE:
<223> OTHER INFORMATION: Description of the artificial sequence:
      primer

<400> SEQUENCE: 5

```
cttatcacgc ccgtatcatg                                                  20
```

<210> SEQ ID NO 6
<211> LENGTH: 25
<212> TYPE: DNA
<213> ORGANISM: Artificial sequence
<220> FEATURE:
<223> OTHER INFORMATION: Description of the artificial sequence:
      primer

<400> SEQUENCE: 6

```
ccagtcaaaa ctatcgagct gcaaa                                            25
```

<210> SEQ ID NO 7
<211> LENGTH: 19
<212> TYPE: DNA
<213> ORGANISM: Artificial sequence
<220> FEATURE:
<223> OTHER INFORMATION: Description of the artificial sequence:
      primer

<400> SEQUENCE: 7

```
ttctctatga tggccgcac                                                   19
```

<210> SEQ ID NO 8
<211> LENGTH: 22
<212> TYPE: DNA
<213> ORGANISM: Artificial sequence
<220> FEATURE:
<223> OTHER INFORMATION: Description of the artificial sequence:
      primer

<400> SEQUENCE: 8

```
gcagcgcttc ggagagatgg ag                                               22
```

<210> SEQ ID NO 9
<211> LENGTH: 3761
<212> TYPE: DNA
<213> ORGANISM: Tropheryma whippelii

<400> SEQUENCE: 9

```
atgccaatgt ggcgttataa ctgccccagt gttattcctg taaacgcgcg gggtgctgta     60
aagtgtcgca gcttgctatg ctgccctgga tttgctacaa tcgttctcgc tgtctcgcca    120
cttgccttca tattgcggtc ggctctggct ttgtcggggt ttttcccctc ttgcccgctt    180
```

-continued

| | | |
|---|---|---|
| tgggtgtctt tgtttggggt aggttttttg gcttctgcta agggtaaaag ggtttgtgcg | 240 |
| ataggtcgct cctctctcgg taagatctct gatccgcttg aggttccgaa ccttcttgat | 300 |
| ttgcagctcg atagttttga ctggctcata ggcggcccta ggtggcgcgt cgcccttgat | 360 |
| gcttaccgca aaaatccgtc aggcgcccca attgccgaaa agagtgggct ggatgaggtg | 420 |
| tttgatgaga tatcccccat agaagattcg gctggcaata tgcagcttaa tttctccaag | 480 |
| ccggttctgg aggccgaaga gttgagcgta agggaatgcc gtgttcgagg caggacctat | 540 |
| tcggcgcccc tgtatgttga ggccgagttc atgaatcatg atacgggcga gataagactc | 600 |
| agacggtttt tatgggcgat ttcccgctta tgactgacaa gggtacattc gtcataaacg | 660 |
| gcaccgagag agttgttgtc tctcagcttg ttcgcagccc tggtgtttat tttgagcgca | 720 |
| cgccggaaaa aaacagtgaa aaggatcttt tttcgggcag aataatcccc gctcgcggtg | 780 |
| cttggctaga attcgaagtt gacaggcatg accagcttgg cgttagggtt gacaggaagc | 840 |
| gcaggcagcc ggttattttc tttctgagag caattggcat gactgatgat gagatcaggg | 900 |
| atgcatttgg cgagtttgaa tcaataagcg tccagcacga aagaatatt gggctgtcca | 960 |
| gagatgacgc gctccgggaa atataccgtc gcgttcgtcc gggggagcag gcatcggctg | 1020 |
| aggctgggcg tgcactctta gagaattttt actttaccag cagacgtttt gacctggcaa | 1080 |
| gggttggaag gtacaaagta aatcgcaaac tcggtgttga tgttgatcca actcggatgg | 1140 |
| ttcttacgag gtcggatatt atcgcaacaa ttcgttatct cgcggccttg catctcggtt | 1200 |
| tctccgaggt tgcggtgcta aacagcaaca agagtgtacc aatttcaacc gatgatattg | 1260 |
| accatcttgg taataggcgc attagaccgg ttggtgagtt ggtgcaaaac cagctccggg | 1320 |
| ctggtctggc cagaatggag cgggttgtga gagagcgcat gacaacccag gatatagagg | 1380 |
| cgattatccc gcagacactc ataaatgtca tgccaattgt tgcagcgctg aaggagtttt | 1440 |
| atggcaccag ccagctctcg cagtttatgg atcagaataa ccccccttgcc ggccttacgc | 1500 |
| acaagaggcg cttgtcagct cttggccccg gtggactgtc ccgcgaacgt gccggtgttg | 1560 |
| aggttcgaga cgtaaatccc agtcattacg gcaggatgtg tccgatcgaa accccagaag | 1620 |
| gtccaaatat tggccttata gggtctttag cgtgctattc cagggtgaac agtttcggct | 1680 |
| ttatagaaac cccatataga cgtgttgtca acggaaaagt cacagacgat attgagtata | 1740 |
| tgacagcaac acaggaagat gagcatgcga ttgcccaggc aagcactccg ctgcgaccgg | 1800 |
| acaactcgtt tgttgatgag cgtgttctgg ttcgccgaaa aggtggagag gtcgaggttg | 1860 |
| taccggccga tcaggttgat tatatggatg tgtctggacg tcagatggtg tctgttgcaa | 1920 |
| cttcgcttat acccttcctt gaacataatg acgctaaccg tgctctcatg ggatcgaata | 1980 |
| tgcagagaca ggctgtacca cttctggtta cggagagtcc cctggtcggc acaggtatgg | 2040 |
| agcggtatgt agcgatcgat gcgggtgatg ttttaattgc cgaggatccg ggcattgtgg | 2100 |
| gggatgtttc cgctgatgtt gtcactgtca agcaggatga cgggaaacat cgcgactacc | 2160 |
| atgttggtaa atttgttcgt tcaaatcagg gcaactgtta caaccagcna gttgtggtcc | 2220 |
| gatccggaga tcgtgtagaa aaaggtacag ttcttgcaca tggtccatgt actgacaaag | 2280 |
| gtgagcttag tcttggtaga aatcttctgg ttgctttcat gccctgggag ggctataact | 2340 |
| ttgaggatgc gataattatc agccagaatt tggtcaagga cgacacccct tcgtcaatcc | 2400 |
| acatagaaga acatgaggtt agcacccggg atacgaagct gggcagtgaa gaaataacgc | 2460 |
| gagaccttcc gaatgtaagc atggattaca taaggactt ggacgaacgg ggtattatcc | 2520 |
| ggattggcgc tgaggttggc cctggggaca ttttggttgg taaggtgacc ccaaagggcg | 2580 |

```
agaccgaact cagcgcggaa gagcgtttgc tgagggctat ctttaacgag aagagcatgg    2640
aggttcgcga cacaagtttg aaggtcccac acgggcagca ggggaccgta atcgatgtta    2700
agttgtttga tgcggttgac ggtgaagata agctgggtgc cggcataaat cagcgggttg    2760
ttgtgtacat agcgcataag cgcaagatta cggagggaga taagcttgct gggcgccatg    2820
gcaacaaggg tgttatttca agatccttc cgtagagga tatgcccttc atggctgatg    2880
ggacccccgt tgatataatc cttaatccgc tcggcgtgcc cgcgcgtatg aacttcgggc    2940
aggttttgga aacccatttg gggtggatct ctaagcaagg atggaaaata gagggtgatc    3000
ctgattgggc aaaagatatt cgggtgcgcg aggcgcagcc tgatagtagg gtttcaagtc    3060 cggttttga tggaatttcc gaaggggaga taaccgggct ttttttcttct gtatttccaa    3120 accgtgatgg tgagcgtgct gtcggttctg atggtaaggc tattctctat gatggccgca    3180
cgggggagcc cttcccggaa cctatttccg tcggttacat gtatgtccta aagttgcacc    3240
atctggtaga cgacaagatt catgctcgct caacaggacc gtattcgatg ataacccagc    3300
aaccgctggg cggcaaggca caattcggtg ggcagcgctt cggagagatg gaggtgtggg    3360
cgcttgaggc atatggtgca gcgcacgcac tccaagagtt gctaacaata aagtctgatg    3420
acgttgttgg ccgggtaaag gtatacgatg cgattgtcaa gggttatcca attcctaccc    3480
ccggtgtgcc tgaatcattt aaggttattg tcaaggaaat gcagtctttg tgcataaata    3540
ttgaggttgt ttctgacggt gaggatgatg tttccgctga tgctgaaacc ctacagatag    3600
aagaaggtct ggatacgtct cccaaggtag aagttggttc gcttgaagag gtctagtcgg    3660
gcattcgcaa aagaggtttg ttttgtctac atcttttaaa gaaatccggg ttagtatggc    3720
cacgactgaa gatattcgtc gttggtcata tggcgttgta a                       3761

<210> SEQ ID NO 10
<211> LENGTH: 507
<212> TYPE: DNA
<213> ORGANISM: Tropheryma whippelii

<400> SEQUENCE: 10
ttgagcgcac gccggaaaaa aacagtgaaa aggatctttt ttcgggcaga ataatccccg      60
ctcgcggtgc ttggctagaa ttcgaagttg acaggcatga ccagcttggc gttagggttg     120
acaggaagcg caggcagccg gttatttcct ttctgagagc aattggcatg actgatgatg     180
agatcaggga tgcatttggc gagtttgaat caataagcgt ccagcacgaa aagaatattg     240
ggctgtccag agatgacgcg ctccgggaaa tataccgtcg cgttcgtccg ggggagcagg     300
catcggctga ggctgggcgt gcactcttag agaattttta ctttaccagc agacgtttg     360 acctggcaag ggttggaagg tacaaagtaa atcgcaaact cggtgttgat gttgatccaa     420
ctcggatggt tcttacgagg tcggatatta tcgcaacaat tcgttatctc gcggccttgc     480
atctcggttt ctccgaggtt gcggtgc                                         507

<210> SEQ ID NO 11
<211> LENGTH: 20
<212> TYPE: DNA
<213> ORGANISM: Artificial sequence
<220> FEATURE:
<223> OTHER INFORMATION: Description of the artificial sequence:
      primer

<400> SEQUENCE: 11
ttgagcgcac gccggaaaaa                                                  20
```

<210> SEQ ID NO 12
<211> LENGTH: 20
<212> TYPE: DNA
<213> ORGANISM: Artificial sequence
<220> FEATURE:
<223> OTHER INFORMATION: Description of the artificial sequence:
    primer

<400> SEQUENCE: 12
gcaccgcaac ctcggagaaa                                               20

<210> SEQ ID NO 13
<211> LENGTH: 19
<212> TYPE: DNA
<213> ORGANISM: Artificial sequence
<220> FEATURE:
<223> OTHER INFORMATION: Description of the artificial sequence:
    primer

<400> SEQUENCE: 13
cggaaacatc ccccacaat                                                19

<210> SEQ ID NO 14
<211> LENGTH: 17
<212> TYPE: DNA
<213> ORGANISM: Artificial sequence
<220> FEATURE:
<223> OTHER INFORMATION: Description of the artificial sequence:
    primer

<400> SEQUENCE: 14
accgacgata tcgacca                                                  17

<210> SEQ ID NO 15
<211> LENGTH: 18
<212> TYPE: DNA
<213> ORGANISM: Artificial sequence
<220> FEATURE:
<223> OTHER INFORMATION: Description of the artificial sequence:
    primer

<400> SEQUENCE: 15
ttggtaaggt gaccccaa                                                 18

<210> SEQ ID NO 16
<211> LENGTH: 17
<212> TYPE: DNA
<213> ORGANISM: Artificial sequence
<220> FEATURE:
<223> OTHER INFORMATION: Description of the artificial sequence:
    primer

<400> SEQUENCE: 16
ggtaaagcgc agttcgg                                                  17

<210> SEQ ID NO 17
<211> LENGTH: 17
<212> TYPE: DNA
<213> ORGANISM: Artificial sequence
<220> FEATURE:
<223> OTHER INFORMATION: Description of the artificial sequence:
    primer

<400> SEQUENCE: 17
ccagcccgga gctggtt                                                  17

```
<210> SEQ ID NO 18
<211> LENGTH: 15
<212> TYPE: DNA
<213> ORGANISM: Artificial sequence
<220> FEATURE:
<223> OTHER INFORMATION: Description of the artificial sequence:
      primer

<400> SEQUENCE: 18
tttcatttgc caagc                                                    15

<210> SEQ ID NO 19
<211> LENGTH: 17
<212> TYPE: DNA
<213> ORGANISM: Artificial sequence
<220> FEATURE:
<223> OTHER INFORMATION: Description of the artificial sequence:
      primer

<400> SEQUENCE: 19
ggtaaagcgc agttcgg                                                  17

<210> SEQ ID NO 20
<211> LENGTH: 17
<212> TYPE: DNA
<213> ORGANISM: Artificial sequence
<220> FEATURE:
<223> OTHER INFORMATION: Description of the artificial sequence:
      primer

<400> SEQUENCE: 20
gtcattccaa accgtgg                                                  17

<210> SEQ ID NO 21
<211> LENGTH: 18
<212> TYPE: DNA
<213> ORGANISM: Artificial sequence
<220> FEATURE:
<223> OTHER INFORMATION: Description of the artificial sequence:
      primer

<400> SEQUENCE: 21
ctatgcacgc attagcga                                                 18

<210> SEQ ID NO 22
<211> LENGTH: 16
<212> TYPE: DNA
<213> ORGANISM: Artificial sequence
<220> FEATURE:
<223> OTHER INFORMATION: Description of the artificial sequence:
      primer

<400> SEQUENCE: 22
gaaccgcttg aggttc                                                   16

<210> SEQ ID NO 23
<211> LENGTH: 17
<212> TYPE: DNA
<213> ORGANISM: Artificial sequence
<220> FEATURE:
<223> OTHER INFORMATION: Description of the artificial sequence:
      primer

<400> SEQUENCE: 23
accttcatca tcaacgg                                                  17
```

-continued

```
<210> SEQ ID NO 24
<211> LENGTH: 16
<212> TYPE: DNA
<213> ORGANISM: Artificial sequence
<220> FEATURE:
<223> OTHER INFORMATION: Description of the artificial sequence:
      primer

<400> SEQUENCE: 24
gattcgttgc gggaca                                                      16
```

SEQUENCE OF THE TROPHERYMA WHIPPELII BACTERIA RPOB GENE AND OLIGONUCLEOTIDE FOR MOLECULAR DIAGNOSIS OF WHIPPLE'S DISEASE

BACKGROUND

The present invention relates to the domain of diagnostics. More precisely, the invention relates to molecular diagnostics of Whipple's disease using detection techniques and/or amplification and sequencing techniques by means of oligonucleotide probes or primers, and their application to research on the presence or identification of bacteria of *Tropheryma whippelii* type.

Whipple's disease is a disease present in various forms. The most classic form is that of a fever with chronic diarrhoea resulting in loss of weight, but it is also a disease which is susceptible to giving chronic articular attacks, cerebral attacks with dementia, ophthalmologic attacks with uveity and also cardiac arrest, in particular endocarditis with negative haemoculture. Ever since it was described in 1907, Whipple evokes the existence of a bacteria associated with <<intestinal lipodystrophy>> before observation of numerous micro-organisms after silvery coloration of a mesenteric ganglion [Whipple GH (1907) Bull. John Hopkins Hosp. 18: 328]. Bringing to the for of the positive non-specific PAS character (from the English <<periodic acid Schiff>>) of this bacteria, then the observations by electronic microscopy, confirm the presence of an intracellular bacterial species having a positive Gram structure [Chears et al. (1961) Gastroenterology 41:1296]. The universal molecular tool 16S RNAr has helped confirm this hypothesis by specifying the phylogenic taxonomy of this novel bacterial species, and by assigning it the provisional name of *Tropheryma whippelii* to evoke the notion of intestinal malabsorption and honor the discoverer of the ailment [Reiman D. et al. (1992) N. Engl. J. Med. 327:293]. The direct sequencing of 721 bases of a fragment amplified from a biopsy of the small intestine of a patient [Wilson K H et al. (1991) Lancet 338:474], then from a ganglion of another patient [Wilson K H et al. (1992) ASM News 58:318] confirms the originality of the bacterial species associated with Whipple's disease. The sequencing by Relman et al. (op. cite) of 1321 bases representing 90% of the 16S rDNA gene on a sample, and a fragment of 284 bases in four other patients has helped confirm that the bacterial species associated with Whipple's disease represented a new species, specify its taxonomic position in the phylum of actinomycetes, that is, bacteria having a positive Gram structure with a high content of guanosine plus cytosine, representing a new branching relatively close to two known species in human pathology, *Acfinomyces pyogenes* and *Rothia dentocariosa*.

The rpoB gene codes one of the sub-units of bacterial RNA polymerase and constitutes a genetic marker allowing specific detection of the bacteria of the species *Tropheryma whippelii*.

According to Lazcano et al. [J. Mol. Evol. (1988) 27:365–376], the RNA polymerases are divided into two groups according to their origin, with one constituted by the viral RNA- or DNA-dependent RNA polymerases, and the other constituted by the DNA-dependent RNA polymerases of eukaryotic or prokaryotic origin (archaebacteria and eubacteria). The eubacterial DNA-dependent RNA polymerases are characterized by a simple and conserved multimeric constitution known as <<core enzyme>>, represented by αββ', or <<holoenzyme>> represented by αββ'δ [Yura and Ishihama, Ann. Rev. Genet. (1979) 13:59–97].

Numerous works have brought the functional role to the fore, within the multimeric enzymatic complex, of the β sub-unit of the eubacterial RNA polymerase. The archaebacterial and eukaryotic RNA polymerases present, for their part, a more complex structure of up to ten, even thirty sub-units [Puhlet et al. Proc. Natl. Acad. Sci. USA (1989) 86:4569–4573].

The genes which code the different sub-units αββ'δ of the DNA-dependent RNA polymerase in eubacteria, respectively the rpoA, rpoB, rpoC and rpoD genes, are classed in different groups comprising the genes coding for proteins constituting the ribosomal sub-units or for enzymes implied in the replication and reparation of the genome [Yura and Yshihma, Ann. Rev. Genet. (1979) 13:59–97]. Certain authors have shown that the sequences of the rpoB and rpoC genes could be utilized to construct phylogenetic trees [Rowland et al. Biochem. Soc. Trans. (1992) 21:40S] allowing the different branchings and sub-branchings to be separated among the kingdoms of the living.

Diagnosis of the disease is currently undertaken by observation, after coloration, of microscopic smears obtained from biopsy or by amplification and sequencing of the universal gene tool 16S RNAr (Relman et al., op. cite).

All the same, the 16S gene is a moderately discriminating gene for the identification of the bacteria. In addition, it is necessary to employ several molecular targets for identifying the bacteria, especially to eliminate problems of molecular contamination.

Furthermore, this bacteria was for the first time isolated and cultivated in cellular systems in the laboratory of the inventors [Raoult D. et al. (2000) N. Engl. J. Med. 342:620 and WO 00158440] from the cardiac valve removed from a patient presenting with endocarditis with negative haemoculture (Twist clone).

SUMMARY

The inventors have already described in WO-A-00/58440 a fragment of 612 bases of the rpoB gene of the *Thropheryma whippelii* bacteria corresponding to SEQ ID No. 3 from which they had determined two specific nucleotide sequences of the rpoB gene of *Tropheryma whippelii* usable as specific amplification primers and specific detection probes of the *Tropheryma whippelii* species.

The techniques described in WO-A-00/58440 did not however aid in obtaining the complete sequence of the rpoB gene of *Tropheryma whippelii*.

An aim of the present invention is to provide additional fragments of the rpoB gene, especially the complete sequence of the rpoB gene of *Tropheryma whippelii*, in particular to supply specific novel sequences of the rpoB gene of *Tropheryma whippelii*; more particularly still, sequences having a greater detection specificity than the sequences drawn from the fragments SEQ ID No. 3 described in WO-A-00/58440.

Several attempts to extend the sequence SEQ ID No. 3 with consensus primers originating from rpoB gene of other bacteria and specific primers developed by the inventors (SEQ ID No. 13, 15 and 17) have succeeded in extending the sequence only as far as obtaining the sequence SEQ ID No. 4 of 2750 Pb described hereinafter, but have not then aided in obtaining the complete sequence of the gene. The inventors have developed a series of specific primers to put into use in the technique known as <<walk on the genome>> (<<Genome Walker>> described in Siebert et al Nucleic Acids Research 23:10871088, 1995) from determining a series of specific amplification primers, namely the amplification primers identified hereinafter as SEQ ID No. 5 to 8. These different amplification primers have step by step allowed fragments more and more distant from SEQ ID No. 4 to be obtained, as far as obtaining the complete sequence SEQ ID No. 9.

The object of the present invention therefore is the complete sequence of the rpoB gene of the *Tropheryma whippelii* bacteria constituted by the sequence SEQ ID No. 9. The complete sequence of the rpoB gene was determined by the combination of two techniques, [enzymatic amplification and direct automatic sequencing with consensus primers between a large number of other bacteria, of different genre and species on the one hand; and by direct automatic sequencing from amplification products obtained after application of the Genome Walker technique (walk on the genome) to the DNA extracted from the first Twist clone of *Tropheryma whippelii*, on the other hand. This latter technique consists of walking along the gene from a first known fragment by creating a partial bank of the chromosomal DNA of the bacteria being studied. This technique, to be described hereinbelow, thus requires a quantity of chromosomal bacterial DNA which can be obtained only after extraction of said DNA from a pure bacterial culture and it supposes availability of an isolate in culture. It is the availability of this isolate and the determination of the different amplification primers SEQ ID No. 5 to 8 from SEQ ID No. 4 which enabled successful application of the genome walker technique for determining the complete sequence of the rpoB gene in a Twist clone of the *Tropheryma whippelii* bacteria.

The present invention therefore also relates to sequences of nucleic acids of the species *Tropheryma whippelii*, whereof the nucleotide sequence is included in the sequence SEQ ID No. 9 of the gene rpoB of said bacteria indicated above and not fully included in the SEQ ID No. 3, or a complementary sequence of said nucleotide sequence.

From the complete sequence SEQ ID No. 9, the inventors have in fact determined a sequence SEQ ID No. 10 of greater specificity vis-à-vis the rpoB gene of *Tropheryma whippelii* outside the zone corresponding to SEQ ID No. 3, from which they were able to determine two particular specific sequences framing a fragment of around 500 pairs of bases, namely the sequences SEQ ID No. 11 and 12 imparting optimal reliability for the specific detection of the bacteria *Tropheryma whippelii* by amplification and sequencing of the amplification product or by hybridization for the detection probe.

An object of the present invention is thus a monocatenary oligonucleotide selected from those oligonucleotides having a sequence of at least 10 consecutive nucleotide units included in a sequence selected among:

the sequence SEQ ID No. 9 and not fully included in the sequence SEQ ID No. 3 and preferably not included in SEQ ID No. 3, and preferably one of the sequences SEQ ID No. 10, SEQ ID No. 11 and SEQ ID No. 12, and the complementary sequences of these oligonucleotides.

A more particularly preferred oligonucleotide has a sequence selected among the complete sequences SEQ ID No. 11 and SEQ ID no. 12 and their complementary sequences.

The object of the present invention is also an oligonucleotide which has a sequence selected among:

the sequences of at least 10 consecutive nucleotides included in a sequence selected by the sequences SEQ ID No. 5 to 8 and SEQ ID No. 17, and their complementary sequences, and preferably, said complete sequences SEQ ID No. 5 to 8 and SEQ ID No. 17 and their complementary sequences.

In particular the oligonucleotides according to the present invention have at least 10 nucleotide units such as described hereinabove and at most 100, preferably at most 50 units. More particularly, an oligonucleotide according to the present invention preferably has from 12 to 35 units, preferably still from 18 to 22.

The nucleotide sequences according to the present invention can be prepared by chemical synthesis using techniques well known to the expert and described for example in the article by Itakura K. et al. [(1984) Annu. Rev. Biochem. 53: 323].

A first application of an oligonucleotide according to the present invention is its utilization as a species probe for the detection, in a biological sample, of bacteria of the species *Tropheryma whippelii*. In the following description, such a probe according to the present invention will be called a species probe.

Preferably a species probe according to the present invention is constituted by an oligonucleotide selected from:

those oligonucleotides having a nucleotide sequence of at least 10 consecutive nucleotides included in one of the sequences SEQ ID No. 10, SEQ ID No. 11 and SEQ ID No. 12, and their complementary sequences, and those oligonucleotides having a nucleotide sequence selected among the complete sequences SEQ ID No. 11 and SEQ ID No. 12 and their complementary sequences.

The probes according to the present invention can be employed, for diagnostic purposes, in the search for the presence or absence of a nucleic acid target in a sample, according to all known hybridization techniques and especially techniques of punctual deposit on filter, known as <<DOTBLOT" [Maniatis et al. (1982) Molecular Cloning, Cold Spring Harbor], DNA transfer techniques known as <<SOUTHERN BLOT" [Southern E. M., J. Mol. Biol. (1975) 98:503], RNA transfer techniques known as <<NORTHERN BLOT>>, or techniques known as <<sandwich>>, with a sensor probe and/or a detection probe, said probes being capable of hybridizing with two different regions of the nucleic acid target, and one at least of said probes (generally the detection probe) being capable of hybridizing with a region of the target which is specific to the species, it being understood that the sensor probe and the detection probe must have nucleotide sequences which are at least partially different.

The nucleic acid to be detected (target) can be obtained following classic amplification, that is, giving DNA, obtained after amplification by PCR, or RNA, obtained following transcriptional amplification by TAM, NASBA, 3SR etc . . . . In the case of detection of a target of double-line nucleic acid type, it is appropriate proceed with denaturising of the latter before putting the detection process to use. The nucleic acid target can be obtained by extraction according to known methods of nucleic acids of a sample to be examined. The denaturising of a double-line nucleic acid can be carried out using known methods of chemical, physical or enzymatic denaturising, and in particular by heating at an appropriate temperature, greater than 80° C.

In order to implement the above-mentioned hybridization techniques, and in particular the <<sandwich>> techniques, a probe according to the present invention, called a sensor probe, is immobilized on a solid support, and another probe according to the present invention, called a detection probe, is marked with a marker agent. The examples of support and marker agent are such as defined previously.

Another object of the invention is a process for determining the presence or the absence of a *Tropheryma whippelii* bacteria in a sample containing or likely to contain nucleic acids of at least one such bacteria, comprising the stages consisting of placing said sample in contact with at least one species probe according to the present invention, then determining in a manner known per se the formation or absence of formation of a hybridization complex between said probe and the nucleic acid of the sample.

Examples of detection of the formation or absence of formation of a hybridization complex between said probe and the nucleic acid comprise <<DOT-BLOT>>, <<SOUTHERN-BLOT>> and <<sandwich>> techniques.

In accordance with a particular embodiment of this process for determining the presence or the absence of a species of *Tropheryma whippelii*, several species probes according to the present invention are used, it being understood that said probes are capable of hybridizing with non-overlapped regions of a nucleic acid corresponding to the rpoB gene of *Tropheryma whippelii*.

In an advantageous manner, a species probe is immobilized on a solid support, and another probe is marked by a marker agent, known as a detection probe, which is not necessarily a species probe.

Another application of an oligonucleotide according to the present invention is its use as a nucleotide primer which can be used in the synthesis of a nucleic acid of *Thropheryma whippelii* in the presence of a polymerase by a process known in and of itself, especially in amplification methods using such synthesis in the presence of a polymerase (PCR, RT-PCR, etc . . . ). In particular, a primer according to the present invention can be utilized for specific inverse transcription of a sequence of messenger RNA of *Tropheryma whippelii* to obtain a corresponding complementary DNA sequence. Such inverse transcription can constitute the first stage of the RT-PCR technique, the following stage being amplification by PCR of the complementary DNA obtained. The primers according to the present invention can also be utilized for specific amplification by chained polymerization reaction of the total sequence of the DNA of the rpoB gene of *Tropheryma whippelii*.

According to a particular case said primer comprising an oligonucleotide according to the present invention comprises in addition the forward or reverse sequence of a promoter recognized by a RNA polymerase (promoters T7, T3, SP6 for example [Studier FW, BA Moffatt (1986) J. Mol. Biol. 189:113]: such primers can be used in amplification processes of nucleic acid inserting a transcription step, such as, for example, NASBA or 3SR techniques [Van Gemen B. et al. Abstract M A 1091, 7th International Conference on AIDS (1991) Florence, Italy].

More particularly, an object of the invention is a nucleotide primer which can be used for total or partial sequencing of the rpoB gene of any clone of *Tropheryma whippelii*, preferably a specific sequence of the rpoB gene of *Thropheryma whippelii*. In particular, the nucleotide primer can be used for the sequencing of an amplified nucleic acid. The sequencing is obtaining the total or partial sequence of the rpoB gene by a process known per se, abortive polymerization using di-deoxynucleotides [Sanger F., Coulson AR (1975) J. Mol. Biol. 94:441] or multiple hybridizations using DNA chips.

Preferably, when used as a primer for sequencing a specific sequence of the rpoB gene of *Thropheryma whippelii*, an oligonucleotide is used which is constituted by:
  oligonucleotides having a nucleotide sequence of at least 10 consecutive nucleotides included in one of the sequences SEQ ID No. 10, SEQ ID No. 11 and SEQ ID No. 12, and their complementary sequences, and
  oligonucleotides having a nucleotide sequence selected from among the complete sequences SEQ ID No. 11 and SEQ ID No. 12 and their complementary sequences.

The present invention accordingly also provides a process for determining the presence or absence of a *Tropheryma whippelii* bacteria in a sample containing, or capable of containing, nucleic acids of at least one such bacteria, wherein amplification of the DNA of the sample is carried out by means of two primers according to the present invention and the resulting sequence is compared to the sequence SEQ ID No. 9.

Plus particularly, the sequence of the resulting amplification product is compared by running its sequencing in advance.

Preferably, amplification of the DNA of the sample is carried out by means of the two primers SEQ ID No. 11 and 12 and the resulting sequence is compared to the sequence SEQ ID No. 10.

BRIEF DESCRIPTION OF THE DRAWINGS

The invention will be better understood by means of the following description, divided into two examples, which relate to experiments carried out with the aim of realizing the invention and which are given purely by way of illustration and explanation.

DETAILED DESCRIPTION OF EMBODIMENTS

Figure 1:
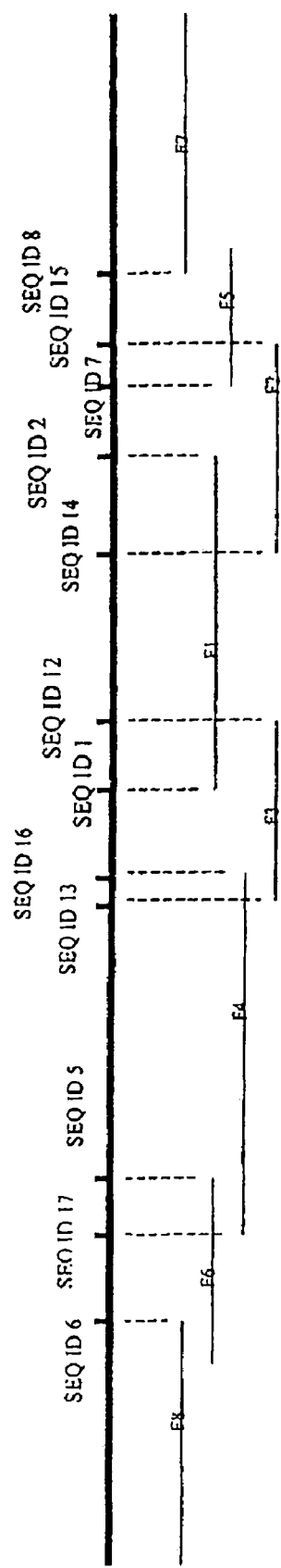
FIG. 1 shows the positions of the specific and consensual primers utilized to determine successive fragments of the complete rpoB gene of the bacterial species *Tropheryma whippelii*.

Different terms, utilized in the description and the claims, are defined hereinbelow:
  <<nucleic acid extract of bacteria>> is understood to mean either total nucleic acid, or genomic DNA, or messenger RNA, or again the DNA obtained from inverse transcription of the Messenger RNA, or again ribosomal RNA;
  a <<nucleotide fragment>> or an <<oligonucleotide>> are two synonymous terms designating linking of nucleotide units characterized by an informational sequence of natural nucleic acids (or optionally modified) and capable of hybridizing, such as natural nucleic acids, with a complementary nucleotide or substantially complementary fragment, under the strictest preset conditions. The linking can contain nucleotide units of a structure different to that of the natural nucleic acids. A nucleotide fragment (or oligonucleotide) can contain for example up to 100 nucleotide units. It generally contains at least 10, and in particular at least 12 nucleotide units and can be obtained from a natural molecule of nucleic acid and/or by genetic recombination and/or by chemical synthesis, a nucleotide unit is derived from a monomer which can be a natural nucleotide of nucleic acid whereof the constitutive elements are a sugar, a phosphate group and a nitrogenous base selected from among adenine, guanine, uracil, cytosine, thymine; or else the monomer is a nucleotide modified in at least one of the three foregoing constitutive elements; by way of example, modification can intervene either at the level of the bases, with modified bases such as inosine, methyl-5-desoxycytidine, desoxyuridine, dimethylamino-5-desoxyuridine or any other modified base capable of hybridization, either at the level of the sugar, for example replacement of at least one desoxyribose by a polyamide (Nielsen P E et al., Science (1991) 254: 14971500], or again at the level of the phosphate group, for example by replacement by esters selected especially from among diphosphates, alkylphosphonates and phosphorothioates, <<hybridization>> is understood to mean the process during which, under appropriate conditions, two nucleotide fragments having sufficiently complementary sequences are capable of being associated by stable and specific hydrogen bonds, to form a double-line. The conditions of hybridization are determined by the <<stringency>>, that is, the rigor of operating conditions. Hybridization is all the more specific since it is carried out with the highest stringency. The stringency is a function especially of the composition in bases of a probe/target duplex, as well as by the degree of mismatching between two nucleic acids. The stringency can also be a function of the parameter of the hybridization reaction, such as concentration and type of ionic species present in the hybridization solution, the nature and concentration of denaturing agents and/or the hybridization temperature. The stringency of the conditions in which a hybridization reaction must be carried out depends especially on the probes being used. All these data are well known and the appropriate conditions can optionally be determined in each case by routine experiments. In general, according to the length of the probes used, the temperature for the hybridization reaction is included between around 20 and 65° C., in particular between 35 and 65° C. in a saline solution at a concentration of around 0.8 to 1 M.

a <<probe>> is a nucleotide fragment comprising for example from 10 to 100 nucleotide units, especially from 12 to 35 nucleotide units, having a hybridization specificity in conditions determined to form a hybridization complex with a nucleic acid having, in the present case, a nucleotide sequence included either in messenger RNA, or in DNA obtained by inverse transcription of said Messenger RNA, the transcription product; a probe can be utilized for diagnostic purposes (especially sensor or detection probes) or for therapeutic purposes, a <<sensor probe>> is immobilized or immobilisable on a solid support by any appropriate means, for example by covalence, by adsorption, or by direct synthesis on a solid. Examples of supports comprise microtitration plates and DNA chips, or magnetic particles, such as those described in WO 6 A-99/35500.

a <<detection probe>> can be marked using a marker agent selected for example from among radioactive isotopes, enzymes, in particular those enzymes capable of acting on a chromogenic, fluorigenic or luminescent substrate (especially a peroxydase or an alkaline phosphatase), chromophorous chemical compounds, chromogenic, fluorigenic or luminescent compounds, analogues of nucleotide bases and ligands such as biotin, a <<species probe>> is a probe allowing the species of a bacteria to be identified, a <<primer>> is a sequence comprising for example 10 to 100 nucleotide units and having a hybridization specificity under conditions determined for initiation of enzymatic polymerization, for example in an amplification technique such as PCR, in a sequencing process, in a transcription method, etc.

EXEMPLE 1

Complete Sequence of the rpoB Gene of *Tropheryma whippelii*

The complete sequence of the rpoB gene of *Tropheryma whippelii* was determined by the successive combination of two techniques, enzymatic amplification and direct automatic sequencing using consensus primers in the first instance, then the genome walker technique in the second instance.

1—Enzymatic Amplification Associated with Automatic Sequencing

The consensus primers resulting in a first fragment of the *Tropheryma whippelii* rpoB sequence were determined from the comparison of the rpoB sequences of *Bacillus subtilis*, *Bartonella henselae*, *Borrelia burgdorferi*, *Buchnera aphidicola*, *Chlamydia pneumoniae*, *Chlamydia trachomatis*, *Coxiella burnetii*, *Escherichia coli*, *Haemophilus influenzae*, *Helicobacter pylori*, *Legionella pneumophila*, *Mycobacterium leprae*, *Mycobacterium smegmatis*, *Mycobacterium tuberculosis*, *Mycoptasma gailisepticum*, *Mycoplasma genitalium*, *Mycoplasma pneumoniae*, *Neisseria meningitidis*, *Pseudomonas putida*, *Rickettsia prowazekii*, *Rickettsia typhi*, *Salmonella enterica Typhimurium*, *Spiroplasma citri*, *Staphylococcus aureus*, *Synechocystis* spp., *Thermotoga maritima*, *Treponema pallidum*, and Human Granulocytic Ehrlichiosis agent. These sequences were selected by aligning the sequences of the DNA of the rpoB gene of these other different bacteria and by selecting those which were the most preserved with on the hypothesis that they were also present in the rpoB gene of *Tropheryma whippelii*. The primers utilized had the sequence:

SEQ ID no. 1=5'-TIA TGG GII CIA AIA TGC A-3' (position 1967–1985)

SEQ ID no. 2=5'-GCC CAI CAT TCC ATI TCI CC-3' (position 31983217, reverse), in which I represents inosine.

The numeration of the positions mentioned hereinabove and hereinafter correspond to positions on the complete sequence SEQ ID No. 9.

These primers have aided in amplification then sequencing of a fragment of 1400 pairs of bases of which 612 pairs of bases have been sequenced by means of the primers SEQ ID no. 1 and SEQ ID no. 2 and correspond to the sequence SEQ ID no. 3 (positions 2063–2673) whereof the sequence is

SEQ ID N° 3: 5'-GAGTCCCCTGGTCGGCACAGGTATGGAGCGGTATGTAGCGATCGATGCGGG

TGATGTTTTAATTGCCGAGGATCCGGGCATTGTGGGGATGTTTCCGCTGAT

GTTGTCACTGTCAAGCAGGATGACGGGAAACATCGCGACTACCATGTTGGTA

AATTTGTTCGTTCAAATCAGGGCAACTGTTACAACCAGCNAGTTGTGGTCCGA

TCCGGAGATCGTGTAGAAAAAGGTACAGTTCTTGCACATGGTCCATCATACTGA

CAAAGGTGAGCTTAGTCTTGGTAGAAATCTTCTGGTTGCTTTCATGCCCTGGG

AGGGCTATAACTTTGAGGATGCGATAATTATCAGCCAGAATTTGGTCAAGGAC

GACACCCTTTCNTCAATCCACATAGAAGAACATGAGGTTAGCACCCGGGATAC

GAAGCTGGGCAGTGAAGAAATAACGCGAGACCTTCCGAATGTAAGCATGGAT

TACATAAAGGACTTGGACGAACGGGGTATTATCCGGATTGGCGCTGAGGTTG

GCCCTGGGGACATTTTGGTTGGTAAGGTGACCCCAAAGGGCGAGACCGAAC

TCAGCGCGGAAGAGCGTTTGCTGAGGGCTATCTTT-3'

The sequencing of this first fragment F1 enabled specific amplification primers to be determined which, combined in PCR amplification reactions with degenerated consensual primers, enabled the sequence SEQ ID no. 3 to be extended at its ends 3' and 5' and helped to obtain three other fragments overlapping F2, F3 and F4 for a total length of 2750 pairs of bases corresponding to SEQ ID No. 4. The position of the primers and of the fragments is indicated in FIG. 1. The fragment F3 (positions 1248 to 2163) was obtained by application of the primers SEQ ID No. 13 (specific primer; positions 2145 to 2163): 5'-CGG AAA CAT CCC CCA CAA T-3' and SEQ ID No. 14 (consensual primer; positions 1248 to 1264): 5'-ACC GAC GAT ATC GAC CA-3'; the fragment F2 (positions 2592 to 3229) was obtained by application of the primers SEQ ID No. 15 (specific primer; positions 2592 to 2610): 5'-TTG GTA AGG TGA CCC CAA A-3' and SEQ ID No. 16 (consensual primer; positions 3213 to 3229): 5'-GGT AAA GCG CAG TTC GG-3'; the fragment F4 (positions 484 to 1331) was obtained by application of the primers SEQ ID No. 17 (specific primer; positions 1315 to 1331): 5'-CCA GCC CGG AGC TGG TT-3' and SEQ ID No. 18 (consensual primer; positions. 484 to 498): 5'-TTT CAT TTG CCA AGC-3'.

SEQ ID N° 4: 5'-ATCCCCCATAGAAGATTCGGCTGGCAATATGCAGCTTAATTTCTCCAAGCCGG

TTCTGGAGGCCGAAGAGTTGAGCGTAAGGGAATGCCGTGTTCGAGGCAGGA

CCTATTCGGCGCCCCTGTATGTTGAGGCCGAGTTCATGAATCATGATACGGGC

GAGATAAGACTCAGACGGTTTTTATGGGCGATTTCCCGCTTATGACTGACAAG

GGTACATTCGTCATAAACGGCACCGAGAGAGTTGTTGTCTCTCAGCTTGTTC

GCAGCCCTGGTGTTTATTTTGAGCGCACGCCGGAAAAAACAGTGAAAAGGA

TCTTTTTTCGGGCAGAATAATCCCCGCTCGCGGTGCTTGGCTAGAATTCGAA

GTTGACAGGCATGACCAGCTTGGCGTTAGGGTTGACAGGAAGCGCAGGCAG

CCGGTTATTTTCTTTCTGAGAGCAATTGGCATGACTGATGATGAGATCAGGGA

TGCATTTGGCGAGTTTGAATCAATAAGCGTCCAGCACGAAAAGAATATTGGGC

TGTCCAGAGATGACGCGCTCCGGGAAATATACCGTCGCGTTCGTCCGGGGG

AGCAGGCATCGGCTGAGGCTGGGCGTGCACTCTTAGAGAATTTTTACTTTAC

CAGCAGACGTTTTGACCTGGCAAGGGTTGGAAGGTACAAAGTAAATCGCAAA

CTCGGTGTTGATGTTGATCCAACTCGGATGGTTCTTACGAGGTCGGATATTAT

CGCAACAATTCGTTATCTCGCGGCCTTGCATCTCGGTTTCTCCGAGGTTGCG

GTGCTAAACAGCAACAAGAGTGTACCAATTTCAACCGATGATATTGACCATCTT

GGTAATAGGCGCATTAGACCGGTTGGTGAGTTGGTGCAAAACCAGCTCCGG

GCTGGTCTGGCCAGAATGGAGCGGGTTGTGAGAGAGCGCATGACAACCCAG

GATATAGAGGCGATTATCCCGCAGACACTCATAAATGTCATGCCAATTGTTGCA

-continued

```
GCGCTGAAGGAGTTTTATGGCACCAGCCAGCTCTCGCAGTTTATGGATCAGA
ATAACCCCCTTGCCGGCCTTACGCACAAGAGGCGCTTGTCAGCTCTTGGCCC
CGGTGGACTGTCCCGCGAACGTGCCGGTGTTGAGGTTCGAGACGTAAATCC
CAGTCATTACGGCAGGATGTGTCCGATCGAAACCCCAGAAGGTCCAAATATT
GGCCTTATAGGGTCTTTAGCGTGCTATTCCAGGGTGAACAGTTTCGGCTTTAT
AGAAACCCCATATAGACGTGTTGTCAACGGAAAAGTCACAGACGATATTGAGT
ATATGACAGCAACACAGGAAGATGAGCATGCGATTGCCCAGGCAAGCACTCC
GCTGCGACCGGACAACTCGTTTGTTGATGAGCGTGTTCTGGTTCGCCGAAAA
GGTGGAGAGGTCGAGGTTGTACCGGCCGATCAGGTTGATTATATGGATGTGT
CTGGACGTCAGATGGTGTCTGTTGCAACTTCGCTTATACCCTTCCTTGAACAT
AATGACGCTAACCGTGCTCTCATGGGATCGAATATGCAGAGACAGGCTGTAC
CACTTCTGGTTACGGAGAGTCCCCTGGTCGGCACAGGTATGGAGCGGTATGT
AGCGATCGATGCGGGTGATGTTTTAATTGCCGAGGATCCGGGCATTGTGGGG
GATGTTTCCGCTGATGTTGTCACTGTCAAGCAGGATGACGGGAAACATCGCG
ACTACCATGTTGGTAAATTTGTTCGTTCAAATCAGGGCAACTGTTACAACCAG
CNAGTTGTGGTCCGATCCGGAGATCGTGTAGAAAAAGGTACAGTTGTTGCAC
ATGGTCCATGTACTGACAAAGGTGAGCTTAGTCTTGGTAGAAATCTTCTGGTT
GCTTTCATGCCCTGGGAGGGCTATAACTTTGAGGATGCGATAATTATCAGCCA
GAATTTGGTCAAGGACGACACCCTTTCGTCAATCCACATAGAAGAACATGAG
GTTAGCACCCGGGATACGAAGCTGGGCAGTGAAGAAATAACGCGAGACCTTC
CGAATGTAAGCATGGATTACATAAAGGACTTGGACGAACGGGGTATTATCCGG
ATTGGCGCTGAGGTTGGCCCTGGGGACATTTTGGTTGGTAAGGTGACCCCAA
AGGGCGAGACCGAACTCAGCGCGGAAGAGCGTTTGCTGAGGGCTATCTTTA
ACGAGAAGAGCATGGAGGTTCGCGACACAAGTTTGAAGGTCCCACACGGGC
AGCAGGGGACCGTAATCGATGTTAAGTTGTTTGATGCGGTTGACGGTGAAGA
TAAGCTGGGTGCCGGCATAAATCAGCGGGTTGTTGTGTACATAGCGCATAAGC
GCAAGATTACGGAGGGAGATAAGCTTGCTGGGCGCCATGGCAACAAGGGTG
TTATTTCAAAGATCCTTCCGGTAGAGGATATGCCCTTCATGGCTGATGGGACC
CCCGTTGATATAATCCTTAATCCGCTCGGCGTGCCCGCGCGTATGAACTTCGG
GCAGGTTTTGGAAACCCATTTGGGGTGGATCTCTAAGCAAGGATGGAAAATA
GAGGGTGATCCTGATTGGGCAAAAGATATTCGGGTGCGCGAGGCGCAGCCT
GATAGTAGGGTTTCAAGTCCGGTTTTTGATGGAATTTCCGAAGGGGAGATAAC
CGGGCTTTATTCTTCTGTATTTCCAAACCGTGATGGTGAGCGTGCTGTCGGTT
CTGATGGTAAGGCTATTCTCTATGATGGCCGCAC-3'
```

The following attempts to extend this sequence by the technique of the consensus primers then failed, not allowing sequencing of the gene to be continued along this approach. In particular, the following consensus primers selected from among the most preserved sequences of the rpoB genes of other bacteria phylogenetically close to *Tropheryma whippelii*: *Mycobacterium smegmatis, Mycobacterium leprae, Mycobacterium tuberculosis, Bacillus licheniformis, Salmonella enterica Typhimurium* were tested without success: Balich7f: 5'-GGT AAA GCG CAG TTC GG-3' (SEQ ID No. 19); Balich460f: 5'-GTC ATT CCA AAC CGT GG-3' (SEQ ID No. 20); Balich37f: 5'-CTA TGC ACG CAT TAG CGA-3' (SEQ ID No. 21); Myco12F: 5'-GAA CCG CTT GAG GTT C-3' (SEQ ID No. 22); Myco43F: 5'-ACC TTC ATC ATC AAC GG-3' (SEQ ID No. 23); Myco8R: 5'-GAT TCG TTG CGG GAC A-3'(SEQ ID No. 24).

2—<<Genome Walker>> Technique

This setback occurring on the clone of *Tropheryma whippelii* in culture explains that it would have been impossible to obtain a fortiori the entirety of the sequence of the rpoB gene of *Tropheryma whippelii* from clinical sampling containing *Tropheryma whippelii* bacteria. A second technique known as <<Genome Walker>> was then applied in order to complete the sequence of *Tropheryma whippelii* rpo8 in the direction 3' and in the direction 5'. This technique has been described [(1995) Siebert et al. Nucl. Acids Res. 23:1087–1088] and consists of creating a bank of the genomic DNA of the bacteria then amplifying fragments of this bank by means of universal primers independent of the desired sequence and of specific primers of the desired sequence. After having extracted a large quantity of DNA (of the order of a microgram) purified from the bacterial Twist clone *Tropheryma whippelii* described in WO 04158440, the bacterial DNA is fragmented by enzymatic digestion by means of restriction endonucleases and the resulting fragments are bound at one of their two ends to synthetic oligonucleotides called adapters provided in a commercial kit (Genome Walker kit®, Clontech Laboratories, Palo Alto, Calif.). Complementary oligonucleotides of the adapters, likewise supplied in the same laboratory kit, then make up amplification primers for the linked enzymatic amplification technique (<<polymerase chain reaction >>, PCR). These oligonucleotides thus constitute universal primers which are utilized in this technique independently of the sequence of bacterial DNA studied. In order to create the PCR reactions, a second oligonucleotide must be incorporated as amplification primer into the PCR reactions. This oligonucleotide primer must respond to several criteria and determining its sequence constitutes an aspect of the invention:

(1) the sequence of this oligonucleotide is complementary to SEQ ID no. 4

(2) this oligonucleotide is positioned at fifty bases from the end of SEQ ID no. 4

(3) this oligonucleotide has a length greater than 20 bases. The utilization of a first oligonucleotide exhibiting these characteristics corresponding to the sequence SEQ ID no. 5=5'CTT ATC TCG CCC GTA TCA TG-3' (position 627–646, inverse) has resulted in a fragment F6 (positions 146 to 646) of 500 pairs of bases. On the base of the resulting sequence, utilization of a second specific oligonucleotide corresponding to the sequence SEQ ID No. 6: =5'-CCA GTC AAA ACT ATC GAG CTG CAA A-3' (position 307–331, inverse) enabled amplification of a fragment F8 of 1100 pairs of bases containing the end 3' of the rpoB gene (positions 1 to 331) and extending downstream of this end. In addition, on the base of the sequence SEQ ID No. 4, the sequence SEQ ID No. 4 has been extended in the direction 5' by using an oligonucleotide SEQ ID No. 7: 5'-TTC TCT ATG ATG GCC GCA C-3' (position 3168–3187) of a fragment F5 (positions 3168 to 3668) of 500 pairs of bases. Finally, on the base of this latter fragment, a specific oligonucleotide was determined having a sequence SEQ ID No. 8: 5'-GCA GCG CTT CGG AGA GAT GGA G-3' (position 3357–3379) which resulted in a fragment F7 of 1500 pairs of bases containing the end 5' of the rpoB gene (positions 3357 to 3657) and extending beyond this end. This genome walking technique assumes obtaining a large quantity of chromosomal DNA of *Tropheryma whippelii* and its application was made possible by obtaining the Twist clone from the *Tropheryma whippelii* bacteria and extraction of a large quantity of DNA from said clone. Obtaining an isolated and cultivated clone of *Tropheryma whippelii* was necessary to determine the entire rpoB sequence in the *Tropheryma whippelii* bacteria.

Amplification of the genomic bank by means of oligonucleotides SEQ No. 5 to SEQ No. 8 enabled the sequence SEQ ID no. 4 to be extended in the directions 3' and 5' so as to obtain the complete sequence of the rpoB gene of *Tropheryma whippelii* Twist clone. The complete sequence of the rpoB gene of *Tropheryma whippelii* obtained by applying the techniques of consensual amplification and genome walking deposited in GenBank with accession number AF243072, corresponds to SEQ ID no. 9. In total, this sequence SEQ ID No. 9 was obtained according to the diagram in FIG. 1 which specifies the position of the consensual primers and the successive fragments obtained:

In the sequence SEQ ID No. 9 represented hereinafter, the sequence SEQ ID No. 4 is underlined, and the sequence in bold characters are in the order:

SEQ ID No. 6 (complementary sequence),
SEQ ID No. 5 (complementary sequence),
SEQ ID No. 11 (identical sequence),
SEQ ID No. 12 (complementary sequence),
SEQ ID No. 7 (identical sequence),
SEQ ID No. 8 (identical sequence),

```
SEQ ID n° 9 = 5'-ATGCCAATGTGGCGTTATAACTGCCCCAGTGTTATTCCTGTAAACGCGCGGG

GTGCTGTAAAGTGTCGCAGCTTGCTATGCTGCCCTGGATTTGCTACAATCGTT

CTCGCTGTCTCGCCACTTGCCTTCATATTGCGGTCGGCTCTGGCTTTGTCGG

GGTTTTTTCCCTCTTGCCCGCTTTGGGTGTCTTTGTTTGGGGTAGGTTTTTTG

GCTTCTGCTAAGGGTAAAAGGGTTTGTGCGATAGGTCGCTCCTCTCTCGGTA

AGATCTCTGATCCGCTTGAGGTTCCGAACCTTCTTGATTTGCAGCTCGATAGT

TTTGACTGGCTCATAGGCGGCCCTAGGTGGCGCGTCGCCCTTGATGCTTACC

GCAAAAATCCGTCAGGCGCCCCAATTGCCGAAAAGAGTGGCCTGGATGAGG

TGTTTGATGAGATATCCCCCATAGAAGATTCGGCTGGCAATATGCAGCTTAAT

TTCTCCAAGCCGGTTCTGGAGGCCGAAGAGTTGAGCGTAAGGGAATGCCGTG

TTCGAGGCAGGACCTATTCGGCGCCCCTGTATGTTGAGGCCGAGTTCATGAA

TCATGATACGGGCGAGATAAGACTCAGACGGTTTTTATGGGCGATTTCCCGC
```

-continued

TTATGACTGACAAGGGTACATTCGTCATAAACGGCACCGAGAGAGTTGTTGTC

TCTCAGCTTGTTCGCAGCCCTGGTGTTTATTTTGAGCGCACGCCGGAAAAAA

ACAGTGAAAAGGATCTTTTTTCGGGCAGAATAATCCCCGCTCGCGGTGCTTG

GCTAGAATTCGAAGTTGACAGGCATGACCAGCTTGGCGTTAGGGTTGACAGG

AAGCGCAGGCAGCCGGTTATTTTCTTTCTGAGAGCAATTGGCATGAGTGATGA

TGAGATCAGGGATGCATTTGGCGAGTTTGAATCAATAAGCGTCCAGCACGAA

AAGAATATTGGGCTGTCCAGAGATGACGCGCTGCGGGAAATATACCGTCGCG

TTCGTCCGGGGAGCAGGCATCGGCTGAGGCTGGGCGTGCACTCTTAGAGA

ATTTTTACTTTACCAGCAGACGTTTTGACCTGGCAAGGGTTGGAAGGTACAAA

GTAAATCGCAAACTCGGTGTTGATGTTGATCCAACTCGGATGGTTCTTACGAG

GTCGGATATTATCGCAACAATTCGTTATCTCGCGGCCTTGCATCTCGGTTTCT
C

CGAGGTTGCGGTGCTAAACAGCAACAAGAGTGTACCAATTTCAACCGATGAT
A

TTGACCATCTTGGTAATAGGCGCATTAGACCGGTTGGTGAGTTGGTGCAAAA

CCAGCTCCGGGCTGGTCTGGCCAGAATGGAGCGGGTTGTGAGAGAGCGCAT

GACAACCCAGGATATAGAGGCGATTATCCCGCAGACACTCATAAATGTCATG
C

CAATTGTTGCAGCGCTGAAGGAGTTTTATGGCACCAGCCAGCTCTCGCAGTT

TATGGATCAGAATAACCCCCTTGCCGGCCTTACGCACAAGAGGCGCTTGTCA

GCTCTTGGCCCCGGTGGACTGTCCCGCGAACGTGCCGGTGTTGAGGTTCGA

GACGTAAATCCCAGTCATTACGGCAGGATGTGTCCGATCGAAACCCCAGAAG

GTCCAAATATTGGCCTTATAGGGTCTTTAGCGTGCTATTCCAGGGTGAACAG
T

TTCGGCTTTATAGAAACCCCATATAGACGTGTTGTCAACGGAAAAGTCACAG
A

CGATATTGAGTATATGACAGCAACACAGGAAGATGAGCATGCGATTGCCCAG
G

CAAGCACTCCGCTGCGACCGGACAACTCGTTTGTTGATGAGCGTGTTCTGGT

TCGCCGAAAAGGTGGAGAGGTCGAGGTTGTACCGGCCGATCAGGTTGATTAT

ATGGATGTGTCTGGACGTCAGATGGTGTCTGTTGCAACTTCGCTTATACCCT
T

CCTTGAACATAATGACGCTAACCGTGCTCTCATGGGATCGAATATGCAGAGA
C

AGGCTGTACCACTTCTGGTTACGGAGAGTCCCCTGGTCGGCACAGGTATGGA

GCGGTATGTAGCGATCGATGCGGGTGATGTTTTAATTGCCGAGGATCCGGGC

ATTGTGGGGATGTTTCCGCTGATGTTGTCACTGTCAAGCAGGATGACGGGA

AACATCGCGACTACCATGTTGGTAAATTTGTTCGTTCAAATCAGGGCAACTG

-continued

T

TACAACCAGCNAGTTGTGGTCCGATCCGGAGATCGTGTAGAAAAAGGTACAG

TTCTTGCACATGGTCCATGTACTGACAAAGGTGAGCTTAGTCTTGGTAGAAA

T

CTTCTGGTTGCTTTCATGCCCTGGGAGGGCTATAACTTTGAGGATGCGATAA

T

TATCAGCCAGAATTTGGTCAAGGACGACACCCTTTCGTCAATCCACATAGAA

G

AACATGAGGTTAGCACCCGGGATACGAAGCTGGGCAGTGAAGAAATAACGCG

AGACCTTCCGAATGTAAGCATGGATTACATAAAGGACTTGGACGAACGGGGT

A

TTATCCGGATTGGCGCTGAGGTTGGCCCTGGGGACATTTTGGTTGGTAAGGT

GACCCCAAAGGGCGAGACCGAACTCAGCGCGGAAGAGCGTTTGCTGAGGG

CTATCTTTAACGAGAAGAGCATGGAGGTTCGCGACACAP.GTTTGAAGGTCC

C

ACACGGGCAGCAGGGGACCGTAATCGATGTTAAGTTGTTTGATGCGGTTGAC

GGTGAAGATAAGCTGGGTGCCGGCATAAATCAGCGGGTTGTTGTGTACATAG

CGCATAAGCGCAAGATTACGGAGGGAGATAAGCTTGCTGGGCGCCATGGCAA

CAAGGGTGTTATTTCAAAGATCCTTCCGGTAGAGGATATGCCCTTCATGGCT

G

ATGGGACCCCCGTTGATATAATCCTTAATCCGCTCGGCGTGCCCGCCCGTAT

GAACTTCGGGCAGGTTTTGGAAACCCATTTGGGGTGGATCTCTAAGCAAGGA

TGGAAAATAGAGGGTGATCCTGATTGGGCAAAAGATATTCGGGTGCGCGAGG

CGCAGCCTGATAGTAGGGTTTCAAGTCCGGTTTTTGATGGAATTTCCGAAGG

GGAGATAACCGGGCTTTTTTCTTCTGTATTTCCAAACCGTGATGGTGACCGTG

CTGTCGGTTCTGATGGTAAGGCTATTCTCTATGATGGCCGCACGGGGGAGCC

CTTCCCGGAACCTATTTCCGTCGGTTACATGTATGTCCTAAAGTTGCACCATCT

GTAGACGACAAGATTCATGCTCGCTCAACAGGACCGTATTCGATGATAACCC

AGCAACCGCTGGGCGGCAAGGCACAATTCGGTGGGCAGCGCTTCGGAGAG

ATGGAGGTGTGGGCGCTTGAGGCATATGGTGCAGCGCACGCACTCCAAGAG

TTGCTAACAATAAAGTCTGATGACGTTGTTGGCCGGGTAAAGGTATACGATGC

GATTGTCAAGGGTTATCCAATTCCTACCCCCGGTGTGCCTGAATCATTTAAGG

TTATTGTCAAGGAAATGCAGTCTTTGTGCATAAATATTGAGGTTGTTTCTGACG

GTGAGGATGATGTTTCCGCTGATGCTGAAACCCTACAGATAGAAGAAGGTCT

GGATACGTCTCCCAAGGTAGAAGTTGGTTCGCTTGAAGAGGTCTAGTCGGGC

ATTCGCAAAAGAGGTTTGTTTTGTCTACATCTTTTAAAGAAATCCGGGTTAGTA

TGGCCACGACTGAAGATATTCGTCGTTGGTCATATGGCGTTGTAA-3'

This sequence measures 3657 pairs of bases and has a cytosine content plus guanosine of 50.4%.

EXAMPLE 2

Specific Detection of the rpoB Gene of *Tropheryma whippelii*

Two specific primers were determined from the SEQ ID no. 9 so as to specifically frame a fragment of 507 pairs of bases of the rpoB gene of *Tropheryma whippelii*, having a sequence SEQ ID No. 10=5'-

1181–1200 of the sequence SEQ ID No. 9 of the rpoB gene of the *Tropheryma whippelii* bacteria. The sequence of these two primers is as follows:

SEQ ID n° 11 = 5'-TTG AGC GCA CGC CGG AAA AA-3'

SEQ ID n° 12 = 5'-GCA CCG CAA CCT CGG AGA AA-3'
(inverse complementary primer)

The region of the rpoB gene of *Tropheryma whippelii* framed by these two primers, a region called SEQ ID No. 10 (position 713–1200) shows the highest rate of discrimina-

SEQ ID N° 10 = 5'-TTGAGCGCACGCCGGAAAAAAACAGTGAAAAGGATCTTTTTTCGTCGGGCAGAAT

AATCCCCGCTCGCGGTGCTTGGCTAGAATTCGAAGTTGACACGCATGACCAG

CTTGGCGTTAGGGTTGACAGGAAGCGCAGGCAGCCGGTTATTTTCTTTCTGA

GAGCAATTGGCATGACTGATGATGAGATCAGGGATGCATTTGGCGAGTTTGAA

TCAATAAGCGTCCAGCACGAAAAGAATATTGGGCTGTCCAGAGATGACGCGC

TCCGGGAAATATACCGTCGCGTTCGTCCGGGGAGCAGGCATCGGCTGAGG

CTGGGCGTGCACTCTTAGAGAATTTTTACTTTACCAGCAGACGTTTTGACCTG

GCAAGGGTTGGAAGGTACAAAGTAAATCGCAAACTCGGTGTTGATGTTGATC

CAACTCGGATGGTTCTTACGACGTCGGATATTATCGCAACAATTCGTTATCTCG

CGGCCTTGCATCTCGGTTTCTCCGAGGTTGCGGTGC-3'

These two primers SEQ ID No. 11 and SEQ ID No. 12 were determined in silico so as to respect constraints peculiar to the molecular identification primers. The thesis of these constraints is an integral part of the inventive process in that it is not currently available in the scientific literature: (1) length of 18–22 pairs of bases (2) sequences of the two primers exhibiting an adjacent melting temperature (3) sequences of the two primers allowing neither auto-hybridization nor complementarity (4) sequence framed by these two specific primers of the *Tropheryma whippelii* bacteria; this condition is verified after alignment of the SEQ ID no. 9 with all the sequences of the bacterial rpoB genes available in the information databanks; (5) sequence framed by these two primers having an optimal length of around 500 pairs of bases; this optimal length corresponding to a compromise between the search of an identification region which is the longest possible, thus allowing the greatest discrimination possible between any sequence originating from the SEQ ID no. 9 and all the known homologue bacterial rpoB sequences and the search of an identification region which is the shortest possible, in order to as far as augment the sensitivity of the molecular detection. It is in fact accepted that there is an inverse relation between sensitivity of detection and the length of the sequence of bacterial DNA to be detected in a sampling. Finally, the size of 500 pairs of bases corresponds to the average sequence length obtained after a run on a currently available automatic sequencer. These two primers are localized respectively in position 713–745 and tion, namely a homology percentage less than 70% relative to the other regions of the same gene, including relative to the region SEQ ID No. 3 having a homology percentage of 75 to 85%.

It is important to maintain the highest rate of discrimination in order to take into consideration the margin of error introduced during manipulation of the samples in diagnostic laboratory practice and which result from errors in amplification made by the thermostable polymerases, in particular the Taq polymerase and errors in sequencing. The errors thus introduced are of the order of 0.5%.

Figure 2:
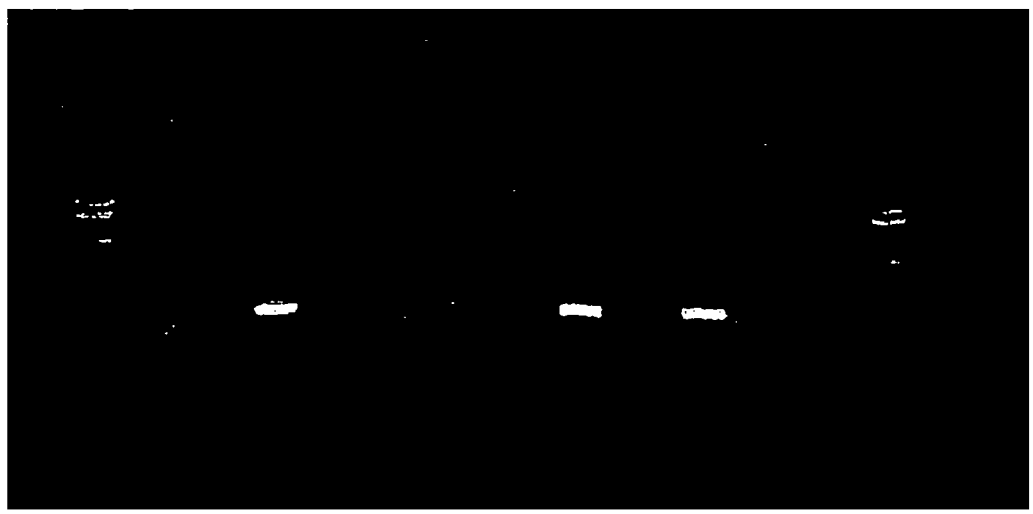
FIG. 2 shows the visualization of the amplification products obtained by means of the primers SEQ ID No. 11 and 12 visualized by coloration in ethidium bromide after electrophoresis on an agar gel of Example 2.

The rpoB gene was amplified by the PCR technique using 35 amplification cycles each comprising a denaturising phase of 94° C. over 30 seconds, a hybridization phase of the primers SEQ ID no. 11 and 12 to 58° C. over 30 seconds and an elongation phase at 72° C. over 60 seconds. The amplification product is visualized after coloration ethidium bromide (FIG. 2). The bacteria controls: *Mycobacterium avium, Mycobacterium tuberculosis, Nocardia otitidiscaviarum, Escherichia coli, Staphylococcus epidermidis, Corynebacterium amycolatum* have not been amplified by the oligonucleotide primers SEQ ID no. 11 and 12, demonstrating the specificity of these primers on bacterial species phylogenetically close to *Tropheryma whippelii*. This technique was applied to the detection of the presence and the absence of the rpoB gene of *Tropheryma whippelii* in ten jejunal biopsies obtained in ten different patients whereof three biopsies had previously been shown to contain the DNA of *Tropheryma whippelii* independently and whereof seven had been shown to be exempt from the DNA of *Tropheryma whippelii*. This technique was applied blind after coding of the ten samplings, with the testers not knowing the code and therefore not knowing the quality of the processed samplings. This technique aided in detecting 100% of true positives and 100% of true negatives. The amplification products obtained for the three positive biopsies were sequenced and the three resulting sequences had 100% homology with SEQ ID no. 10.

FIG. 2 illustrates the PCR amplification products obtained from ten jejunal biopsies taken from patients presenting with confirmed Whipple's disease (columns D, I and K) and not presenting with Whipple's disease (columns C, E, F, G, H, J, and L). Columns A and N represent the marker of molecular weight, columns B and M correspond to the negative amplification test specimens (sterile water). The amplification products are obtained after incorporation of the primers SEQ ID no. 11 and no. 12 according to the present invention and are visualized by coloration with ethidium bromide following electrophoresis on an agar gel.

The invention claimed is:

1. An isolated nucleic acid sequence of the rpoB gene of *Tropheryma whippelii* bacteria, comprising at least one of: the nucleotide sequence set forth in SEQ ID NO: 9 and a full length complement thereof.

2. A process for determining the presence of bacteria of the species *Tropheryma Whippelii* in a biological sample, comprising:
   placing said biological sample in contact with at least one probe consisting of an oligonucleotide consisting of 10–100 contiguous nucleotides of the portions of SEQ ID NO: 9 outside SEQ ID NO: 3, and
   detecting formation or absence of formation of a hybridization complex between said probe and a nucleic acid of said sample, wherein the formation or absence of formation of said hybridization complex determines, respectively, the presence or absence of said bacteria in said sample.

3. The process according to claim 2, wherein said probe consists a nucleotide sequence selected from the group consisting of SEQ ID NOs: 5–8, 10, 11, 12, and 17, and full length complementary sequences of SEQ ID NOs: 10, 11, 12.

4. The process according to claim 2, wherein said probe consists of a nucleotide sequence selected from the group consisting of SEQ ID NOs: 11, 12, and full length complementary sequences of SEQ ID NOs: 11, 12.

5. An amplification primer set comprising at least one forward primer and at least one reverse primer, wherein each primer is 18–35 bases in length, wherein the primers are non-complementary to one another, wherein the primers have corresponding melting temperatures, and wherein the primers together frame an about 500 base region of nucleotides 1–2014 and 2625–3767 of SEQ ID NO: 9, the sequence of said region hybridizing specifically to *Thropheryma whippelii*.

6. The amplification primer set of claim 5, wherein the forward primer and the reverse primer together frame SEQ ID NO: 10.

7. The amplification primer set of claim 5, wherein the forward primer consists of SEQ ID NO: 11, and wherein the reverse primer consists of SEQ ID NO:12.

8. An amplification primer set, comprising at least one forward primer and at least one reverse primer wherein each primer is 18–35 bases in length, consisting of contiguous nucleotides of the portion of SEQ ID NO: 9 outside SEQ ID NO: 3, said contiguous nucleotides forming a sequence hybridizing specifically to *Thropheryma whippelii*.

9. A process for determining the presence or absence of a bacteria of the species *Tropheryma Whippelii* in a biological sample, comprising
   carrying out amplification of DNA of said sample by the means of the primer set of claim 5, and
   detecting formation or absence of formation of an amplified DNA, wherein the formation or absence of formation of said amplified DNA determines, respectively, the presence or absence of said bacteria.

10. The process according to claim 9, wherein wherein the forward primer and the reverse primer together frame SEQ ID NO: 10.

11. The process according to claim 9, wherein wherein the forward primer consists of SEQ ID NO: 11, and wherein the reverse primer consists of SEQ ID NO:12.

12. A process according to claim 9, wherein the sequence of said amplified DNA is compared to the sequence set forth in SEQ ID NO: 9 and the presence or absence of the sequence of the amplified DNA in the sequence set forth in SEQ ID NO: 9 determines, respectively, the presence or absence of said bacteria.

13. A process according to claim 12, wherein the sequence of said amplified DNA is determined in carrying out sequencing of said amplified DNA.

14. A process according to claim 9, wherein said two primers include a primer consisting of the sequence set forth in SEQ ID NO: 11 and a primer consisting of the sequence set forth in SEQ ID NO: 12, and the sequence of the amplified DNA is compared to the sequence set forth in SEQ ID NO: 10 to determine the presence or absence of said bacteria.

15. An oligonucleotide consisting of a sequence selected from the group consisting of SEQ ID NOS: 5–8, 10–12, 17, and full-length complements of SEQ ID NOS: 5–8, 10–12, 17.

16. The oligonucleotide of claim 15, wherein the oligonucleotide is selected from the group consisting of SEQ ID NOS: 5–8, and full-length complements of SEQ ID NOS: 5–8.

17. The oligonucleotide of claim 15, wherein the oligonucleotide is selected from the group consisting of SEQ II) NOS: 10–12 and 17, and full-length complements of SEQ ID NOS: 10–12 and 17.

18. A process for determining the presence or absence of a bacteria of the species *Tropheryma Whippelii* in a biological sample, comprising:
   carrying out amplification of DNA of said sample by the means of the primer set of claim 8, and
   detecting formation or absence of formation of an amplified DNA, wherein the formation or absence of formation of said amplified DNA determines, respectively, the presence or absence of said bacteria.

* * * * *